(12) United States Patent
Shimizu

(10) Patent No.: US 12,279,905 B2
(45) Date of Patent: Apr. 22, 2025

(54) RADIOGRAPHIC IMAGING SYSTEM, METHOD OF CONTROLLING RADIOGRAPHIC IMAGING SYSTEM, AND STORAGE MEDIUM

(71) Applicant: CANON KABUSHIKI KAISHA, Tokyo (JP)

(72) Inventor: Yasutomo Shimizu, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 93 days.

(21) Appl. No.: 17/532,447

(22) Filed: Nov. 22, 2021

(65) Prior Publication Data

US 2022/0167941 A1 Jun. 2, 2022

(30) Foreign Application Priority Data

Nov. 27, 2020 (JP) ................................. 2020-196898

(51) Int. Cl.
*A61B 6/00* (2024.01)
*H04W 4/80* (2018.01)
*H04W 76/14* (2018.01)

(52) U.S. Cl.
CPC .............. *A61B 6/548* (2013.01); *A61B 6/56* (2013.01); *H04W 4/80* (2018.02); *H04W 76/14* (2018.02)

(58) Field of Classification Search
CPC ......... A61B 6/548; A61B 6/56; A61B 6/4283; A61B 6/4452; A61B 6/54; H04W 4/80; H04W 76/14
See application file for complete search history.

(56) References Cited

U.S. PATENT DOCUMENTS

| 2010/0034356 | A1* | 2/2010 | Hayashida | H04L 67/12 378/98 |
| 2011/0150182 | A1* | 6/2011 | Omura | A61B 6/4405 378/116 |
| 2012/0051521 | A1* | 3/2012 | Nishino | A61B 6/461 378/98.5 |
| 2012/0163542 | A1* | 6/2012 | Kitano | A61B 6/56 378/91 |
| 2013/0195251 | A1* | 8/2013 | Saigusa | H05G 1/30 378/101 |
| 2013/0301802 | A1 | 11/2013 | Eguchi | |
| 2013/0329860 | A1* | 12/2013 | Nonaka | H04L 12/12 378/91 |
| 2014/0140634 | A1* | 5/2014 | Hayashida | G06T 5/70 250/336.1 |
| 2014/0177806 | A1 | 6/2014 | Tachikawa | |
| 2014/0295767 | A1* | 10/2014 | Iijima | A61B 6/4283 455/41.3 |

(Continued)

FOREIGN PATENT DOCUMENTS

CN 101369945 A 2/2009
CN 103479371 A 1/2014

(Continued)

*Primary Examiner* — Dani Fox
*Assistant Examiner* — Soorena Kefayati
(74) *Attorney, Agent, or Firm* — Canon U.S.A., Inc., IP Division

(57) ABSTRACT

A radiographic imaging system sets settings for performing wireless communication between a desired radiation control apparatus and a radiographic imaging apparatus without decreasing operator usability.

13 Claims, 8 Drawing Sheets

(56) References Cited

U.S. PATENT DOCUMENTS

| | | | | |
|---|---|---|---|---|
| 2014/0307856 | A1* | 10/2014 | Luthardt | A61B 6/56 378/101 |
| 2015/0078529 | A1 | 3/2015 | Tsubota | |
| 2015/0117426 | A1* | 4/2015 | Okuyama | H04W 36/00837 370/338 |
| 2016/0029991 | A1* | 2/2016 | Tajima | A61B 6/467 250/336.1 |
| 2016/0228087 | A1* | 8/2016 | Oda | A61B 6/5211 |
| 2017/0031035 | A1* | 2/2017 | Ishioka | A61B 6/548 |
| 2017/0079611 | A1* | 3/2017 | Lim | A61B 6/56 |
| 2017/0150939 | A1* | 6/2017 | Shah | A61M 16/202 |
| 2017/0224290 | A1* | 8/2017 | Ishioka | A61B 6/46 |
| 2018/0042096 | A1* | 2/2018 | Kim | H02J 50/10 |
| 2018/0110495 | A1* | 4/2018 | MacLaughlin | A61B 6/545 |
| 2018/0138717 | A1* | 5/2018 | Quigley | A61B 6/032 |
| 2018/0158216 | A1* | 6/2018 | Cao | G01N 23/046 |
| 2018/0174333 | A1* | 6/2018 | Feng | G06T 11/006 |
| 2018/0220988 | A1 | 8/2018 | Jeon | |
| 2019/0166585 | A1* | 5/2019 | Proano | A61B 6/56 |
| 2019/0307413 | A1* | 10/2019 | MacLaughlin | A61B 6/563 |
| 2019/0392940 | A1* | 12/2019 | Suzuki | A61B 6/032 |
| 2020/0008771 | A1* | 1/2020 | Isogai | A61B 6/4233 |

FOREIGN PATENT DOCUMENTS

| | | |
|---|---|---|
| JP | 2009157883 A | 7/2009 |
| JP | 2011120885 A | 6/2011 |
| JP | 2013236711 A | 11/2013 |
| JP | 2014171520 A | 9/2014 |
| JP | 2015083113 A | 4/2015 |
| JP | 2016164776 A | 9/2016 |
| JP | 2017029410 A | 2/2017 |
| JP | 2018196057 A | 12/2018 |
| WO | 2009047994 A1 | 4/2009 |

\* cited by examiner

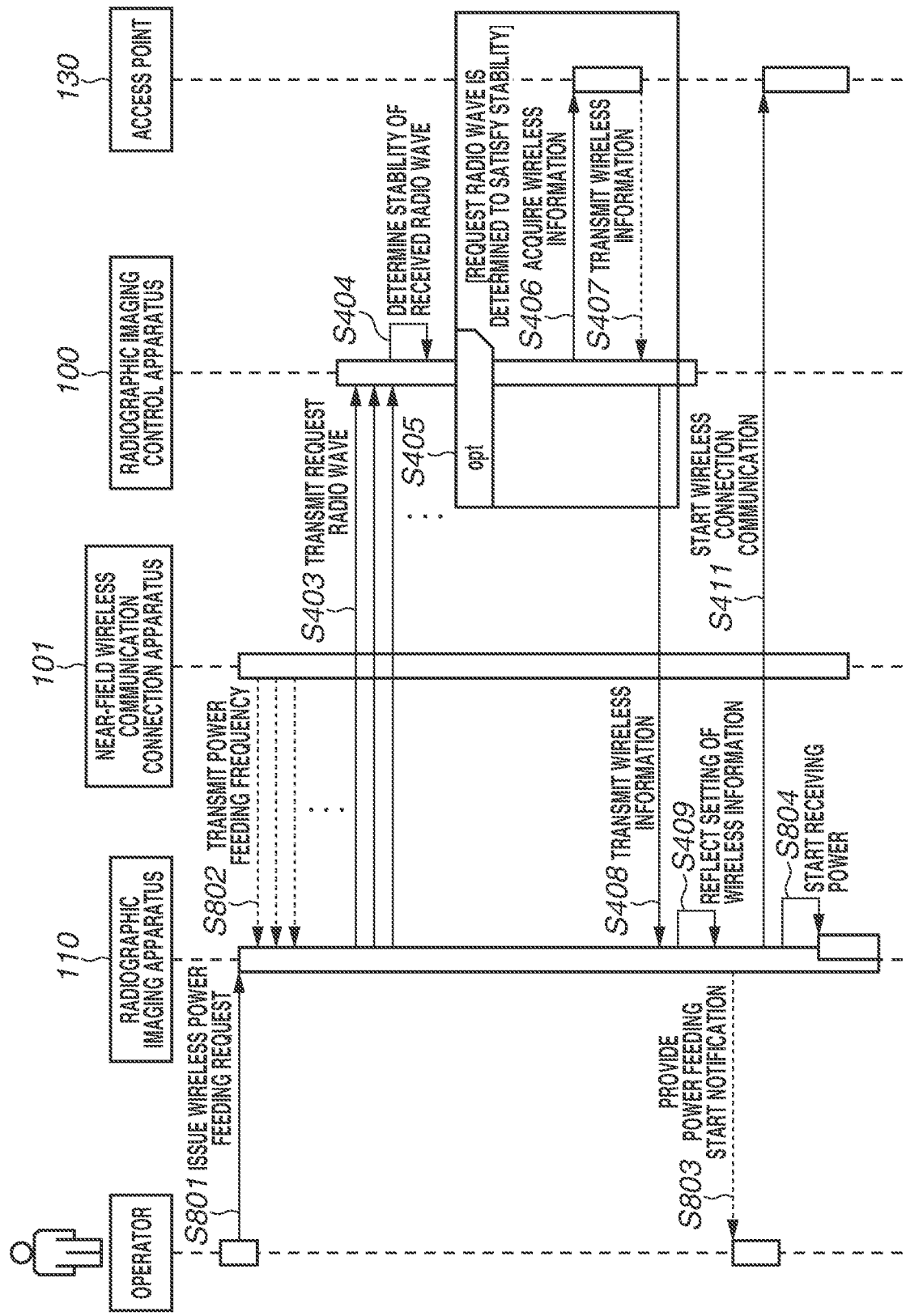

RADIOGRAPHIC IMAGING SYSTEM, METHOD OF CONTROLLING RADIOGRAPHIC IMAGING SYSTEM, AND STORAGE MEDIUM

BACKGROUND

Field

The present disclosure relates to a radiographic imaging system, a method of controlling a radiographic imaging system, and a storage medium.

Description of the Related Art

Imaging systems using radiation are known as radiographic imaging systems in medical fields. As radiographic imaging systems have been digitalized, systems in which a radiographic imaging apparatus generates a digital radiographic image by being irradiated with radiation via a subject, and a radiographic imaging control apparatus checks the image immediately after the radiographic imaging, have been widely used. Such systems realize an improved workflow compared to conventional imaging methods using films, and enable imaging at faster cycles.

Radiographic imaging systems in which a radiographic imaging apparatus and a radiographic imaging control apparatus are wirelessly connected to eliminate the installation limitation of the radiographic imaging apparatus due to a need for cables, have been implemented. To establish a wireless connection between the radiographic imaging apparatus and the radiographic imaging control apparatus, the radiographic imaging apparatus and the radiographic imaging control apparatus to be connected together need to have the same settings for the following: a service set identifier (SSID), an authentication method, an encryption type, and an encryption key. Normally, the apparatuses that are to be connected wirelessly are manually operated to set those settings, or the settings are made using a push button method or a personal identification number (PIN) code method defined by Wi-Fi® Protected Setup (WPS).

However, in a case where the settings are manually made, an input operation is necessary, and there arises a possibility that a connection cannot be established due to an operation error. Similarly, in the PIN code method, an operation of inputting a PIN code to a parent device is necessary. Furthermore, in the push button method, it is necessary to perform an operation different from a normal workflow of a radiographic imaging system, such as an operation of simultaneously pressing or touching a push button of a child device and a push button of a parent device.

Thus, Japanese Patent Application Laid-Open No. 2011-120885 discusses a method of setting wireless communication between a radiographic imaging apparatus and a radiographic imaging control apparatus via a near-field wireless communication connection unit using infrared communication, Bluetooth® communication or another type of communication having a smaller communication range than the wireless communication range. Further, Japanese Patent Application Laid-Open No. 2013-236711 discusses a method of setting a general-purpose SSID to a radiographic imaging apparatus using a near-field wireless communication connection unit, and in a case where a connection is established via a predetermined access point, an SSID of the access point is re-assigned via a management apparatus. This makes it unnecessary for an operator to manually set wireless information.

SUMMARY

Various embodiments of the present disclosure are directed to a radiographic imaging system that allows a setting for performing wireless communication between a desired radiation control apparatus and a radiographic imaging apparatus without decreasing operator usability.

However, the objects of the present disclosure are not limited to the foregoing but include, among other things, producing an operation effect that is derived from a configuration according to each of the below-described example embodiments of the present disclosure, among others, and is not produced by conventional techniques.

According to one embodiment of the present disclosure, a radiographic imaging system includes a radiographic imaging apparatus configured to capture a radiographic image, and a radiographic imaging control apparatus configured to connect to the radiographic imaging apparatus wirelessly and control image capturing performed by the radiographic imaging apparatus. The radiographic imaging control apparatus includes a first communication unit configured to receive a radio wave transmitted from the radiographic imaging apparatus, the radio wave requesting a connection through near-field wireless communication, an acquisition unit configured to acquire wireless information for establishing the wireless connection with the radiographic imaging apparatus in a case where a stability of the received radio wave requesting the connection satisfies a predetermined value, and a second communication unit configured to transmit the wireless information to the radiographic imaging apparatus. The radiographic imaging apparatus includes a transmission unit configured to transmit the radio wave requesting the connection through the near-field wireless communication to the radiographic imaging control apparatus, a setting unit configured to set a setting of the wireless connection based on the wireless information received from the radiographic imaging control apparatus, and an imaging unit configured to capture a radiographic image based on control by the radiographic imaging control apparatus connected based on the setting.

Further features of the present disclosure will become apparent from the following description of example embodiments with reference to the attached drawings.

Various embodiments of the present disclosure allow settings to be made for performing wireless communication between a desired radiographic imaging control apparatus and a radiographic imaging apparatus without decreasing operator usability.

BRIEF DESCRIPTION OF THE DRAWINGS

FIG. 8 is a diagram illustrating an example of a sequence of operation in the radiographic imaging system according to the second example embodiment.

DESCRIPTION OF THE EMBODIMENTS

In a case where a near-field wireless communication connection unit is used as in Japanese Patent Application Laid-Open No. 2011-120885 (described above) and there are a plurality of radiographic imaging control apparatuses, it can be difficult to explicitly control the setting of wireless communication with a desired radiographic imaging control apparatus. Similarly, with the technique discussed in Japanese Patent Application Laid-Open No. 2013-236711 (described above), it can be difficult to control the setting of wireless communication with a desired radiographic imaging control apparatus in a case where there are a plurality of access points.

Further, since a determination regarding whether an emitter of a received signal is within a desired radio range can be made based on the radio wave intensity of the received signal by applying a technique discussed in Japanese Patent Application Laid-Open No. 2015-83113, execution of a near-field wireless communication connection unit can be controlled using the determination. However, the radio wave intensity varies due to an effect of attenuation with distance, so that in a case where a plurality of radiographic imaging control apparatuses is near each other, it is difficult to perform such control. Furthermore, in a case where the radio range is limited to a short range in order to reduce the effect of attenuation of radio wave intensity, it is necessary to perform an operation different from a normal workflow including a process of bringing a radiographic imaging apparatus and a radiographic imaging control apparatus close to each other, and this process decreases operator usability.

Various example embodiments of the present disclosure will be described below with reference to the drawings.

It should be noted that the present invention is not limited to the disclosed specific example embodiments and various modifications and changes are possible without departing from the spirit of the claimed invention.

A first example embodiment will be described below. A system configuration according to the present example embodiment will be described below with reference to FIGS. 1 to 3.

Figure 1:
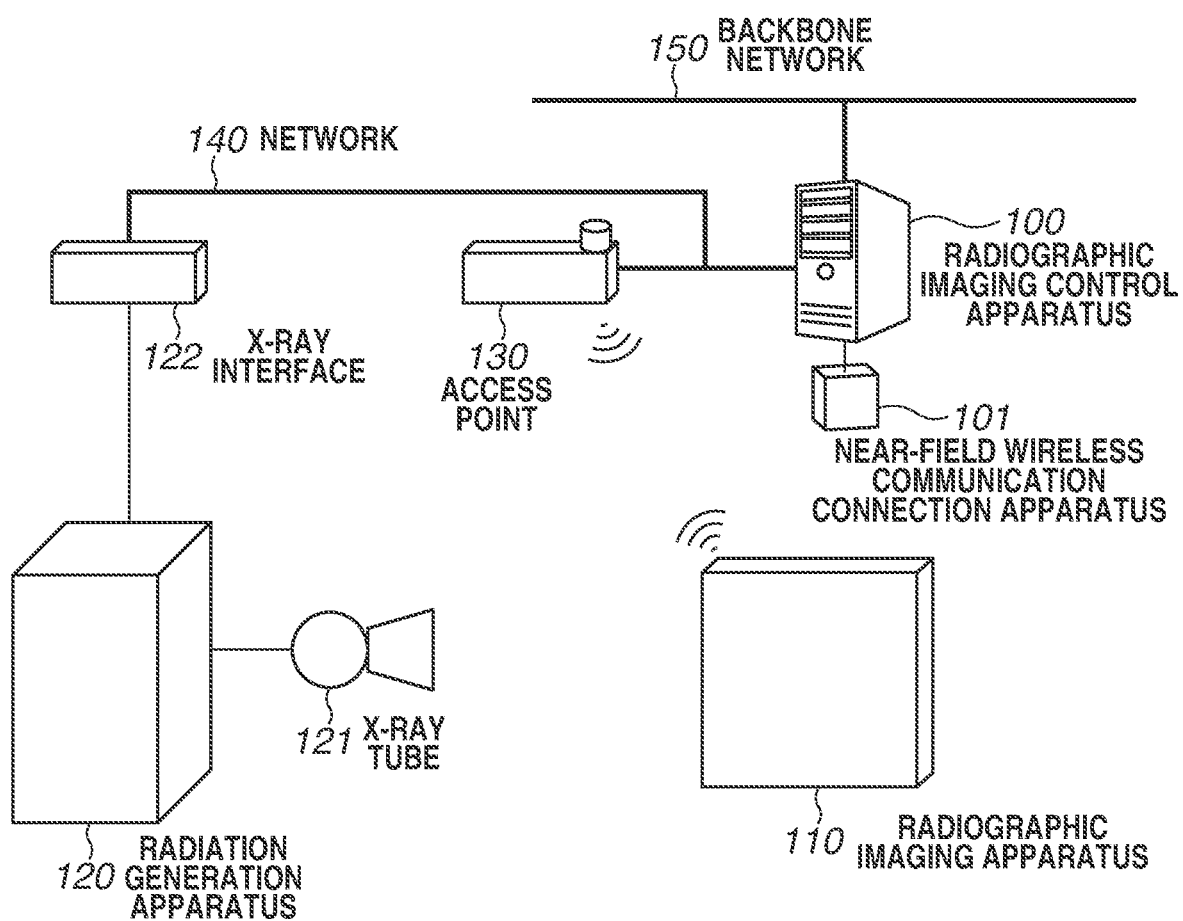
FIG. 1 is a diagram illustrating an example of a system configuration of a radiographic imaging system according to a first example embodiment.

FIG. 1 is a diagram illustrating an example of a configuration of an entire radiographic imaging system according to the present example embodiment. The radiographic imaging system according to the present example embodiment includes a radiographic imaging control apparatus 100, a radiographic imaging apparatus 110, an X-ray interface 122, a radiation generation apparatus 120, and an access point 130. The radiographic imaging system according to the present example embodiment is connected to a network 140 and a main network 150. The main network 150 can be a wired network or a wireless network.

The radiographic imaging control apparatus 100 communicates with the radiographic imaging apparatus 110 via the access point 130 and includes an information processing apparatus such as a computer that controls radiographic imaging.

The radiographic imaging control apparatus 100 also communicates with the radiographic imaging apparatus 110 via a near-field wireless communication connection apparatus 101 and configures settings of communication via the access point 130. According to the present example embodiment, wireless communication that transfers data using radio wave or light within a communication range of several tens of meters is referred to as "near-field wireless communication". The near-field wireless communication connection apparatus 101 can have any configuration for near-field wireless communication and is, for example, an apparatus that uses infrared communication, Bluetooth®, ZigBee®, or Near Field Communication (NFC).

The radiographic imaging control apparatus 100 further communicates with the radiation generation apparatus 120 via the X-ray interface 122 and controls radiographic imaging.

The radiographic imaging apparatus 110 is an apparatus that changes its state to an imaging enabled state in response to an instruction from the radiographic imaging control apparatus 100, performs radiographic imaging in synchronization with the radiation generation apparatus 120, and generates a radiographic image based on radiation emitted from the radiation generation apparatus 120. The number of the radiographic imaging apparatus 110 is not limited to one, and a configuration that uses a plurality of radiographic imaging apparatuses can be employed. Further, while the radiographic imaging apparatus 110 communicates with the radiographic imaging control apparatus 100 through wireless communication using the Institute of Electrical and Electronics Engineers (IEEE) 802.11 standards via the access point 130 according to the present example embodiment, the radiographic imaging apparatus 110 may be connected to the network 140 through wired connection.

The radiation generation apparatus 120 is an apparatus that detects a radiographic operation instruction issued by an operator using an exposure switch (not illustrated) and causes an X-ray tube 121 to generate radiation based on an irradiation condition set via a user input apparatus (not illustrated) such as an operation panel.

Further, the radiation generation apparatus 120 controls execution of the radiographic operation instruction in response to a synchronization instruction from the radiographic imaging control apparatus 100 via the X-ray interface 122.

The access point 130 is an apparatus that performs wireless communication with the radiographic imaging apparatus 110 using the IEEE 802.11 standards and performs wired communication with the radiographic imaging control apparatus 100 via the network 140.

Figure 2:
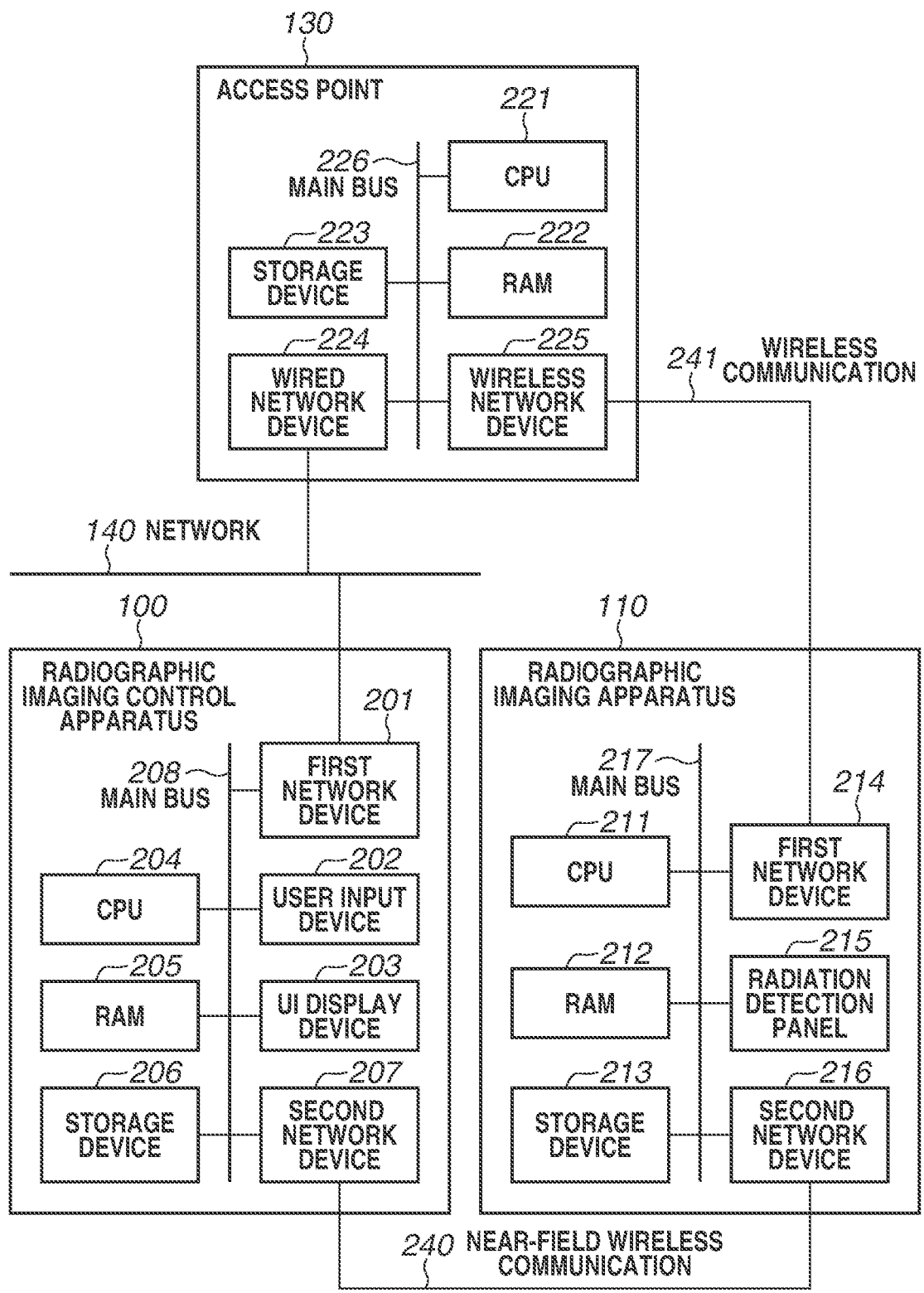
FIG. 2 is a diagram illustrating an example of a hardware configuration of the radiographic imaging system according to the first example embodiment.

FIG. 2 illustrates the radiographic imaging control apparatus 100, the radiographic imaging apparatus 110, and the access point 130 as an example of a hardware configuration of the radiographic imaging system according to the present example embodiment.

The radiographic imaging control apparatus 100 includes a first network device 201, a user input device 202, and a user interface (UI) display device 203. The first network device 201 connects to the network 140. The user input device 202 is, for example, a keyboard and receives user operations. The UI display device 203 is, for example, a liquid crystal display and displays an operation screen and a radiographic image. The radiographic imaging control apparatus 100 further includes a central processing unit (CPU) 204, a random access memory (RAM) 205, and a storage device 206. The CPU 204 controls the entire radiographic imaging control apparatus 100. The RAM 205 provides a workspace for the CPU 204. The storage device 206 stores various control programs and radiographic images received from the radiographic imaging apparatus 110. The radiographic imaging control apparatus 100 further includes a second network device 207. The second network device 207 communicates with the radiographic imaging apparatus 110 through near-field wireless communication 240 based on a communication protocol for near-field wireless communication connection. The components of the radiographic imaging control apparatus 100 are connected together via a main bus 208 and can transmit and receive data to and from one another. While the user input device 202 and the UI display device 203 are described as separate devices, the user input device 202 and the UI display device 203 can be integrated into an operation device.

The radiographic imaging apparatus 110 includes a CPU 211, a RAM 212, and a storage device 213. The CPU 211 controls the entire radiographic imaging apparatus 110. The RAM 212 provides a workspace for the CPU 211. The storage device 213 stores various control programs and generated radiographic images. The radiographic imaging apparatus 110 further includes a first network device 214. The first network device 214 communicates with the access point 130 through wireless communication 241 based on a communication protocol for wireless communication connection. The radiographic imaging apparatus 110 further includes a radiation detection panel 215. The radiation detection panel 215 includes, for example, a flat panel detector (FPD) and generates an electric signal based on the dose of radiation to generate a radiographic image. Further, the radiographic imaging apparatus 110 includes a second network device 216. The second network device 216 communicates with the radiographic imaging control apparatus 100 through the near-field wireless communication 240 based on the communication protocol for near-field wireless communication connection. The components of the radiographic imaging apparatus 110 are connected together via a main bus 217 and can transmit and receive data to and from one another.

The access point 130 includes a CPU 221, a RAM 222, a storage device 223, and a wired network device 224. The CPU 221 controls the entire access point 130. The RAM 222 provides a workspace for the CPU 221. The storage device 223 stores various control programs. The wired network device 224 connects to the network 140. The access point 130 further includes a wireless network device 225. The wireless network device 225 communicates with the radiographic imaging apparatus 110 through the wireless communication 241 based on the communication protocol for wireless communication connection. The components of the access point 130 are connected together via a main bus 226 and can transmit and receive data to and from one another.

Figure 3:
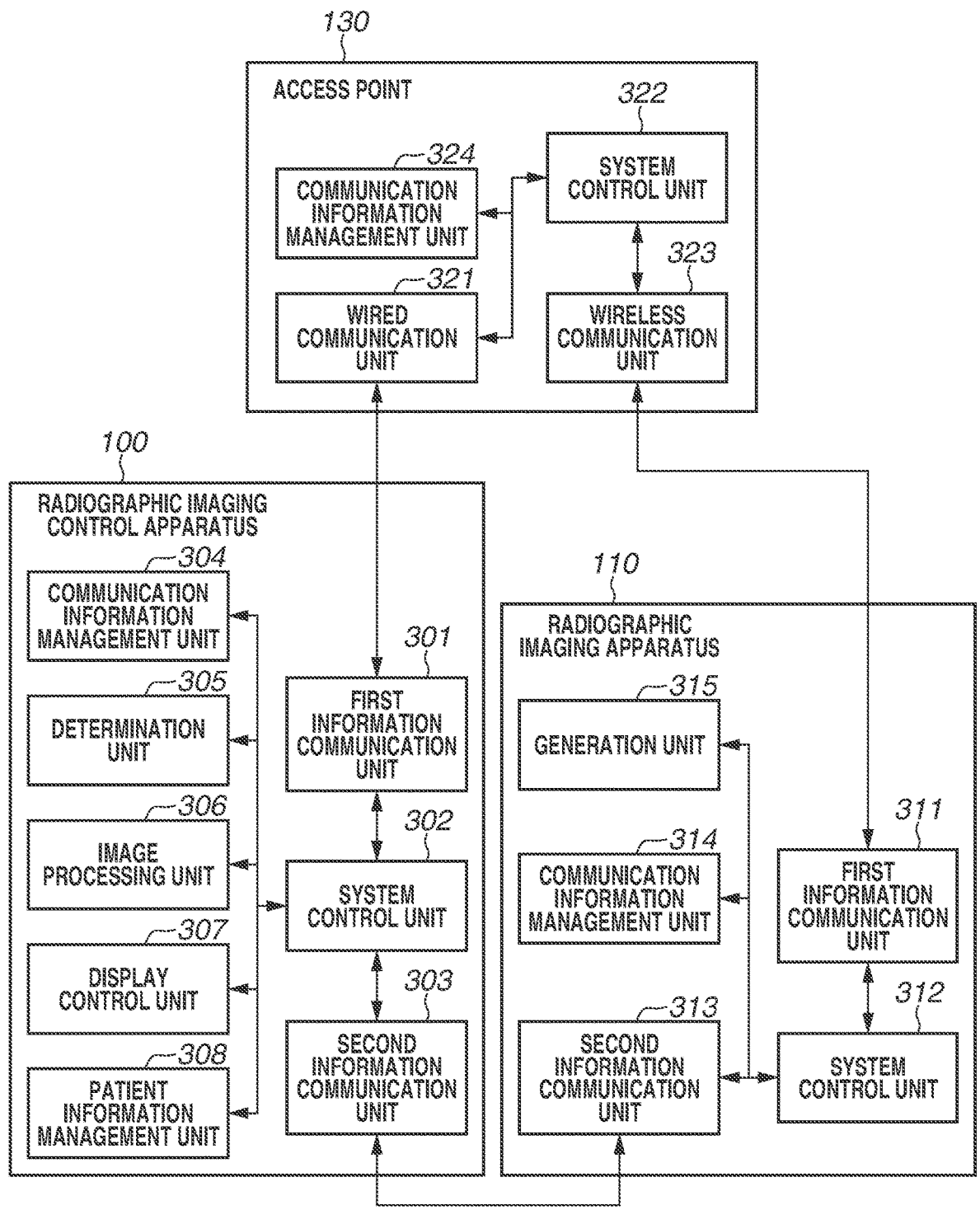
FIG. 3 is a diagram illustrating an example of a software configuration of the radiographic imaging system according to the first example embodiment.

FIG. 3 illustrates the radiographic imaging control apparatus 100, the radiographic imaging apparatus 110, and the access point 130 as an example of a software configuration of the radiographic imaging system according to the present example embodiment.

The CPUs 204, 211, and 221 of the radiographic imaging control apparatus 100, the radiographic imaging apparatus 110, and the access point 130 respectively read control programs stored in the storage devices 206, 213, and 223 onto the RAMs 205, 212, and 222 and execute the read programs to realize the functional units illustrated in FIG. 3.

The radiographic imaging control apparatus 100 includes a first information communication unit 301, a system control unit 302, a second information communication unit 303, a communication information management unit 304, a determination unit 305, an image processing unit 306, a display control unit 307, and a patient information management unit 308.

The first information communication unit 301 is software that controls the first network device 201 to perform communication.

The system control unit 302 performs irradiation control and state management on the radiation generation apparatus 120 and the radiographic imaging apparatus 110 and transmits and receives information about various settings including the access point 130 via the first information communication unit 301 and the second information communication unit 303. The system control unit 302 further acquires a radiographic image from the radiographic imaging apparatus 110 via the first information communication unit 301. The system control unit 302 is a program for realizing basic functions of the radiographic imaging control apparatus 100 and controls operation of each component of the radiographic imaging control apparatus 100.

The second information communication unit 303 is software that controls the second network device 207 to perform communication.

The communication information management unit 304 stores settings for performing communication with the access point 130.

Further, the communication information management unit 304 communicates with the access point 130, acquires wireless information for use in the wireless communication 241, and transmits the acquired wireless information to the radiographic imaging apparatus 110. The wireless information is, for example, information for identifying a communication network such as the access point 130 and includes information about an extended service set identifier (ESSID) or a physical channel. The communication information management unit 304 further manages an identification received in communication through the near-field wireless communication 240, such as a corporate identifier or a unique serial number of the radiographic imaging apparatus 110, in association with the wireless information. The identification is not limited to those described above and can be any information that specifies the manufacturer of the radiographic imaging apparatus 110 or information that identifies each imaging apparatus in a case where there is a plurality of imaging apparatuses.

The determination unit 305 determines whether a request radio wave from the radiographic imaging apparatus 110 to which a connection request is transmitted through the near-field wireless communication 240 includes an identification that identifies the radiographic imaging apparatus 110, such as an identification associated with a manufacturer name or a unique product serial number. For example, in a case where Bluetooth® is employed as a communication method, a radio wave (advertisement packet) has an area for storing a corporate identifier, so that the identification can be associated with the area. Thus, the determination unit 305 determines whether the area of the request radio wave includes the identification. Further, in a case where the area of the request radio wave includes the identification, the determination unit 305 performs reception determination based on stability information about the received radio wave signal. Furthermore, in a case where the area of the request radio wave includes the identification, the determination unit 305 instructs the communication information management unit 304 to acquire the wireless information and transmit the acquired wireless information to the radiographic imaging apparatus 110.

According to the present example embodiment, at least one of the following information is used in determining the stability of the received radio wave signal by the determination unit 305. Specifically, at least one of the signal intensity of the received radio wave, the radio wave reception time of the received radio wave, and range information measured from the received radio wave is used. The configuration, however, is not particularly limited, and any information that depends on the radio wave intensity can be used such as a bit error rate or a radio wave communication speed.

Furthermore, according to the present example embodiment, at least one of the following information is used in determining the stability of the received radio wave signal by the determination unit 305. Specifically, as to the signal intensity of the received radio wave, at least one of information about whether a radio wave with a signal intensity greater than or equal to a predetermined value is received a predetermined number of times or more and information about whether the average of the intensity of the radio wave received the predetermined number of times is greater than or equal to a threshold value is used. As to the radio wave reception time of the received radio wave, at least one of information about whether a radio wave greater than or equal to a threshold value is received a predetermined number of times within a predetermined time and information about whether the average of the reception intervals of the radio wave received the predetermined number of times is within a specified time is used. As to the range information measured from the received radio wave, at least one of information about whether detected range information less than or equal to a predetermined value is detected a predetermined number of times or more and information about whether the average of the detected range information received the predetermined number of times is less than or equal to a threshold value is used. The configuration, however, is not particularly limited, and any evaluation criteria considering the stability dependent on the radio wave intensity can be used such as an evaluation value based on positional information or a statistical measure such as a standard deviation as an evaluation criterion. The threshold value for the radio wave signal is set based on, for example, a radio wave range. The radio wave reception time is specified based on, for example, a radio wave interference status. The number of times of detection of range information is specified based on, for example, a variation in radio wave intensity.

The image processing unit 306 processes a radiographic image acquired via the system control unit 302 and generates an image for use on the radiographic imaging control apparatus 100.

The display control unit 307 displays the image generated by the image processing unit 306 via the UI display device 203. The display control unit 307 further performs processing on an image based on an instruction from the system control unit 302 and switches a screen display on the UI display device 203 based on an operation via the user input device 202.

The patient information management unit 308 manages an imaging order received from a remote installation services (RIS) server (not illustrated) via the main network 150 and controls the radiographic imaging apparatus 110 and the radiation generation apparatus 120 based on the imaging order. Further, the patient information management unit 308 manages the radiographic image generated by the image processing unit 306 and irradiation information (tube voltage, tube current) about the radiation generation apparatus 120 in association with the imaging order and transmits the radiographic image and the irradiation information to an image server (not illustrated) via the main network 150.

The radiographic imaging apparatus 110 includes a first information communication unit 311, a system control unit 312, a second information communication unit 313, a communication information management unit 314, and a generation unit 315.

The first information communication unit 311 is software that controls the first network device 214 to perform communication.

The system control unit 312 receives irradiation control information from the radiographic imaging control apparatus 100 and transmits state management information about the radiographic imaging apparatus 110 to the radiographic imaging control apparatus 100 via the first information communication unit 311. The system control unit 312 also transmits an image generated by the generation unit 315 to the radiographic imaging control apparatus 100 via the first information communication unit 311. Furthermore, the system control unit 312 transmits and receives various types of setting information including the wireless information to and from the access point 130 and the radiographic imaging control apparatus 100 via the first information communication unit 311 and the second information communication unit 313, respectively. The system control unit 312 is a program that realizes basic functions of the radiographic imaging apparatus 110 and controls operation of each component of the radiographic imaging apparatus 110.

The second information communication unit 313 is software that controls the second network device 216 to perform communication.

The communication information management unit 314 communicates with the access point 130 via the first information communication unit 311 through the wireless communication 241. Further, the communication information management unit 314 manages the identification, such as the corporate identifier and the unique serial number, of the radiographic imaging apparatus 110 that is transmitted in communication through the near-field wireless communication 240. The communication information management unit 314 obtains the wireless information such as the ESSID and the physical channel for use in the wireless communication 241 that is received in communication through the near-field wireless communication 240, and the communication information management unit 314 stores the settings.

The generation unit 315 acquires a radiographic image generated with radiation irradiation, corrects the radiographic image using a dark image generated without radiation irradiation, and generates a radiographic image.

The access point 130 includes a wired communication unit 321, a system control unit 322, a wireless communication unit 323, and a communication information management unit 324.

The wired communication unit 321 is software that controls the wired network device 224 and performs wired communication using Ethernet®.

The system control unit 322 controls communication between the radiographic imaging control apparatus 100 and the radiographic imaging apparatus 110 and transmission and reception of various types of setting information about the access point 130 therebetween via the wired communication unit 321 and the wireless communication unit 323. Further, the system control unit 322 is a program for realizing basic functions of the access point 130 and controls operation of each component of the access point 130.

The wireless communication unit 323 is software that controls the wireless network device 225 and performs wireless communication using the IEEE 802.11 standards.

The communication information management unit 324 manages the wireless information that the communication information management unit 324 stores as settings. According to the present example embodiment, the communication information management unit 324 stores the wireless information such as the ESSID and the physical channel for use in the wireless communication 241.

Figure 4:
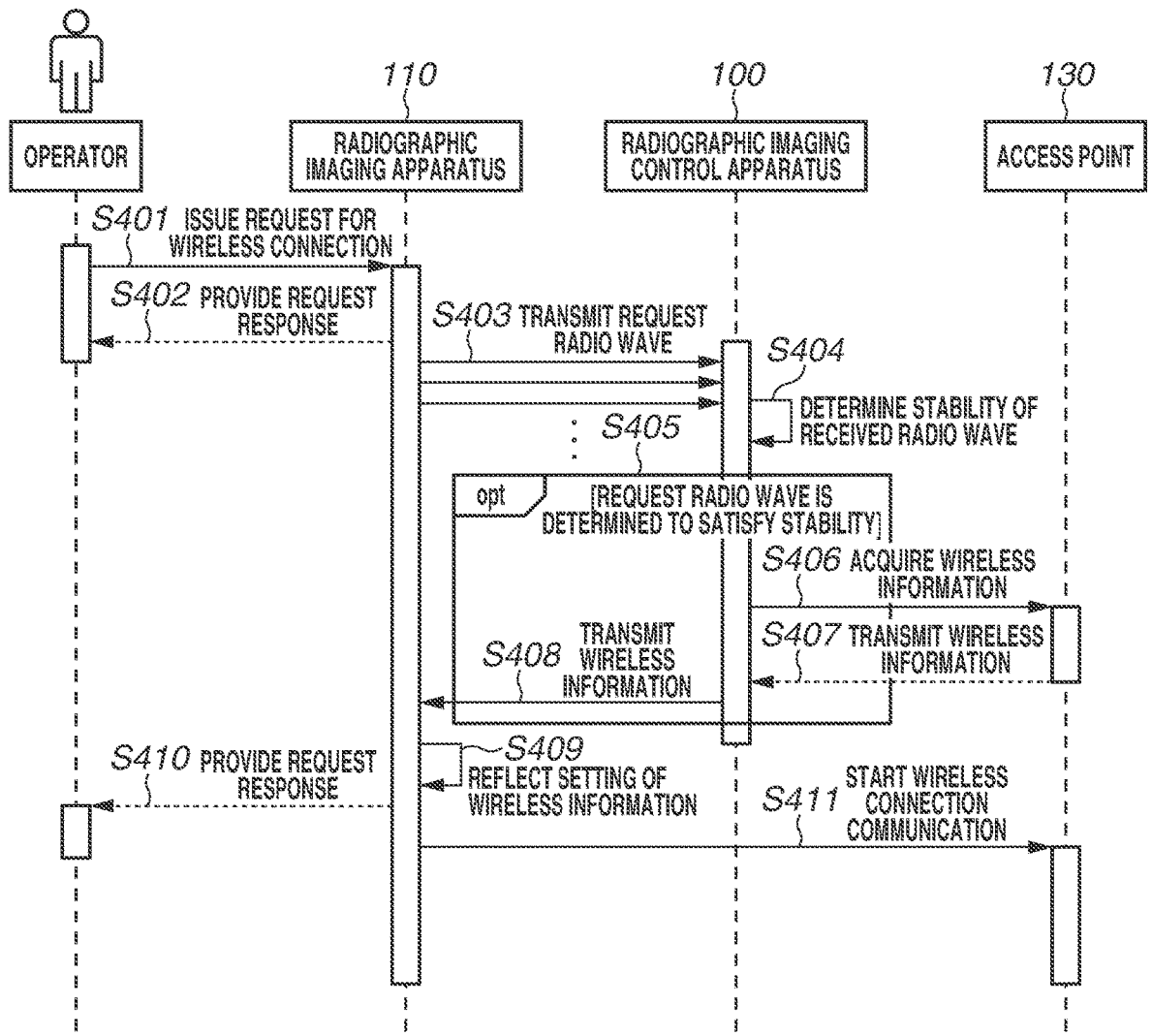
FIG. 4 is a diagram illustrating an example of a sequence of operation in the radiographic imaging system according to the first example embodiment.
Figure 5:
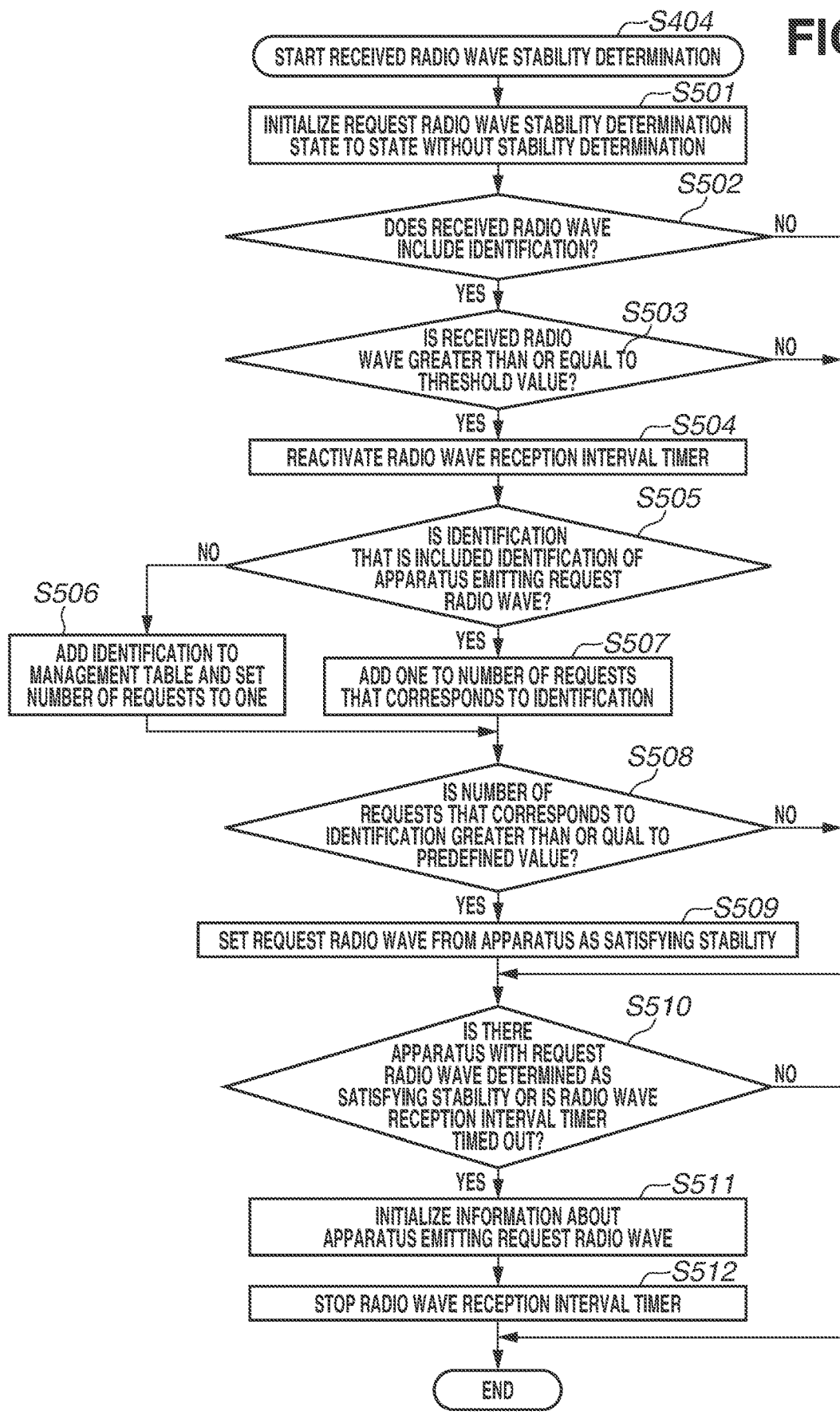
FIG. 5 is a diagram illustrating an example of a flowchart of a radiographic imaging control apparatus according to the first example embodiment.

FIG. 4 illustrates a method for the wireless information communication between the radiographic imaging control apparatus 100 and the radiographic imaging apparatus 110 using the second information communication units 303 and 313 according to the present example embodiment. FIG. 5 illustrates a method of determining the stability of a received radio wave using the determination unit 305 of the radiographic imaging control apparatus 100.

FIG. 4 is a sequence diagram illustrating a wireless information communication process between the radiographic imaging control apparatus 100 and the radiographic imaging apparatus 110 using the second information communication units 303 and 313.

In step S401, an operator (not illustrated) such as a user issues a request for wireless connection to the access point 130 to the radiographic imaging apparatus 110. According to the present example embodiment, the wireless connection request operation is performed by pressing an input portion (not illustrated), such as a button, of the radiographic imaging apparatus 110. The configuration, however, is not particularly limited, and any methods that do not require an operation different from a normal workflow in radiographic imaging can be employed, e.g., an operation of turning on the radiographic imaging apparatus 110 or an operation of inserting the radiographic imaging apparatus 110 into a cradle can be employed. Further, for example, the radiographic imaging apparatus 110 may include a sensor such as a gyro sensor or an acceleration sensor, detect that the operator has moved the radiographic imaging apparatus 110 in a lifting direction, based on a result of measurement by the sensor, and then determine the operation as a wireless connection request operation.

In step S402, the radiographic imaging apparatus 110 provides a request response indicating the receipt of the wireless connection request operation to the operator. According to the present example embodiment, the request response is provided by lighting a display portion (not illustrated), such as a light emitting diode (LED), of the radiographic imaging apparatus 110. The configuration, however, is not particularly limited, and any methods of providing a request response to the operator can be employed, e.g., the radiographic imaging apparatus 110 can output a sound as a request response.

In step S403, the radiographic imaging apparatus 110 transmits a request radio wave to the radiographic imaging control apparatus 100 via the second information communication unit 313. The radiographic imaging apparatus 110 transmits the request radio wave with the identification, such as the corporate identifier and the unique serial number, of the radiographic imaging apparatus 110 included therein. Further, the radiographic imaging apparatus 110 transmits the request radio wave a plurality of times regularly. The intervals of transmission of the request radio wave do not have to be uniform.

In step S404, the radiographic imaging control apparatus 100 receives the request radio wave from the radiographic imaging apparatus 110 via the second information communication unit 303. Here, the radiographic imaging control apparatus 100 further causes the determination unit 305 to determine the stability of the received radio wave via the system control unit 302.

FIG. 5 is a flowchart illustrating the process of determining the stability of the received radio wave by the determination unit 305 of the radiographic imaging control apparatus 100 in step S404. In the present example embodiment, a combination of the determination of whether a radio wave with a predetermined signal intensity is received a specified number of times and the determination of whether a radio wave is received the specified number of times within a predetermined time will be described below as an example of the process of determining the stability of the received radio wave. The process for the stability determination is not limited to that described above, and the stability determination can be performed using, for example, range information measured from a received radio wave.

First, in step S501, the determination unit 305 initializes a state indicating whether the request radio wave from the radiographic imaging apparatus 110 satisfies a stability to a state without stability determination that indicates that there is no radiographic imaging apparatus 110 satisfying the stability. This state is used to indicate a result of the radio wave signal stability determination by the determination unit 305 in a step described below.

Next, in step S502, the determination unit 305 determines whether data storable in the received radio wave from the radiographic imaging apparatus 110 includes the identification. In a case where the determination unit 305 determines that the received radio wave includes the identification (YES in step S502), the processing proceeds to step S503. On the other hand, in a case where the determination unit 305 determines that the received radio wave does not include the identification (NO in step S502), the determination unit 305 determines that the received radio wave is not from a radiographic imaging apparatus, and the processing proceeds to step S510.

Next, in step S503, the determination unit 305 determines whether the radio wave received from the radiographic imaging apparatus 110 is greater than or equal to a predetermined threshold value for radio wave signal intensity. In a case where the determination unit 305 determines that the received radio wave is greater than or equal to the threshold value for radio wave signal intensity (YES in step S503), the determination unit 305 determines that the received radio wave satisfies a stability condition, and the processing proceeds to step S504. On the other hand, in a case where the determination unit 305 determines that the received radio wave is less than the threshold value for radio wave signal intensity (NO in step S503), the determination unit 305 determines that the received radio wave does not satisfy the stability condition, and the processing proceeds to step S510.

Next, in step S504, the determination unit 305 reactivates a radio wave reception interval timer for use in determining whether the radio wave is received the specified number of times within the predetermined time, and the determination unit 305 resets a timer count and restarts counting.

Next, in step S505, the determination unit 305 determines whether the identification included in the radio wave received from the radiographic imaging apparatus 110 is the identification of the radiographic imaging apparatus 110 being emitting a request radio wave received before the received radio wave. In a case where the determination unit 305 determines that the identification included in the received radio wave is the identification of the radiographic imaging apparatus 110 being emitting a request radio wave (YES in step S505), the processing proceeds to step S507.

On the other hand, in a case where the determination unit 305 determines that the identification included in the received radio wave is not the identification of the radiographic imaging apparatus 110 being emitting a request radio wave (NO in step S505), the processing proceeds to step S506.

Next, in step S506, the determination unit 305 adds the identification of the radiographic imaging apparatus 110 to a management table (not illustrated) that manages information about apparatuses emitting request radio waves. Furthermore, the determination unit 305 sets "1" as the number of requests that corresponds to the added identification in the management table (not illustrated) that manages information about apparatuses emitting request radio waves. The number of requests indicates the number of times the request radio wave is received.

Next, in step S507, the determination unit 305 adds one to the number of requests of the request radio wave that corresponds to the identification in the management table (not illustrated) that manages information about apparatuses emitting request radio waves, and sets the addition result as the number of requests.

Next, in step S508, the determination unit 305 determines whether the number of requests that corresponds to the identification in the management table (not illustrated) that manages information about apparatuses emitting request radio waves is greater than or equal to a predefined value. In a case where the determination unit 305 determines that the number of requests that corresponds to the identification is greater than or equal to the predefined value (YES in step S508), the processing proceeds to step S509. On the other hand, in a case where the determination unit 305 determines that the number of requests that corresponds to the identification is less than the predefined value (NO in step S508), the processing proceeds to step S510.

Next, in step S509, the determination unit 305 sets the request radio wave from the radiographic imaging apparatus 110 as satisfying the stability.

Next, in step S510, the determination unit 305 determines whether there is a radiographic imaging apparatus 110 with a request radio wave determined as satisfying the stability by the determination in step S509 or whether the radio wave reception interval timer exceeds a predefined value and is timed out. In a case where the determination unit 305 determines that one of the foregoing conditions is satisfied (i.e., the determination unit 305 determines that the stability is satisfied, or the determination unit 305 determines that the radio wave reception interval timer is timed out) (YES in step S510), the processing proceeds to step S511.

On the other hand, in a case where the determination unit 305 determines that both of the conditions are not satisfied (NO in step S510), the process of determining the stability of the received radio wave ends.

Next, in step S511, the determination unit 305 initializes the setting information in the management table (not illustrated) that manages information about apparatuses emitting request radio waves. Thereafter, the processing proceeds to step S512.

Lastly, in step S512, the determination unit 305 stops the radio wave reception interval timer, and the process of determining the stability of the received radio wave ends.

Returning to the FIG. 4, the rest of the sequence diagram in FIG. 4 will be described below.

In step S405, the radiographic imaging control apparatus 100 refers to the result of the stability determination of the received radio wave made by the determination unit 305 via the system control unit 302 in step S404. In a case where the determination unit 305 determines that the stability is satisfied, the processing proceeds to step S406.

Next, in step S406, the radiographic imaging control apparatus 100 communicates with the access point 130 via the first information communication unit 301 under control by the communication information management unit 304 via the system control unit 302, and acquires the wireless information.

Next, in step S407, the access point 130 transmits the wireless information, such as the ESSID and the physical channel, for use in the wireless communication 241 to the radiographic imaging control apparatus 100.

Thereafter, in step S408, the radiographic imaging control apparatus 100 communicates with the radiographic imaging apparatus 110 via the second information communication unit 303 under control by the communication information management unit 304 via the system control unit 302, and transmits the wireless information.

In step S409, the radiographic imaging apparatus 110 reflects the settings of the wireless information received from the radiographic imaging control apparatus 100 via the second information communication unit 313, using the communication information management unit 314 via the system control unit 312.

In step S410, the radiographic imaging apparatus 110 provides a request response indicating the completion of the wireless connection request operation to the operator. According to the present example embodiment, the request response is provided by lighting the display portion (not illustrated), such as a LED, of the radiographic imaging apparatus 110. The configuration, however, is not particularly limited, and any methods of providing a request response to the operator can be employed, e.g., the radiographic imaging apparatus 110 can output a sound as a request response.

In step S411, the radiographic imaging apparatus 110 starts wireless connection communication with the access point 130 via the second information communication unit 313 based on the settings of the communication information management unit 314. After step S411, a wireless connection is established between the radiographic imaging apparatus 110 and the access point 130 through the wireless communication 241, and the radiographic imaging apparatus 110 and the radiographic imaging control apparatus 100 can communicate with each other.

As described above, according to the first example embodiment, the radiographic imaging control apparatus 100 causes the determination unit 305 to determine the signal stability of the wireless information request radio wave from the radiographic imaging apparatus 110. In a case where the determination unit 305 determines that the radio wave signal is stable, the wireless information is transmitted to the radiographic imaging apparatus 110 and reflected to the settings. Specifically, settings for performing wireless communication between a desired radiographic imaging control apparatus and a radiographic imaging apparatus can be configured in consideration of an effect of a variation in radio wave intensity, without a decrease in operator usability that can be caused by limiting the radio range to the short range.

Next, a second example embodiment of the present disclosure will be described below.

With the configuration according to the first example embodiment, the operator such as the user issues a request for a wireless connection to the access point 130 to the radiographic imaging apparatus 110 by pressing the input portion (not illustrated), such as the button, of the radiographic imaging apparatus 110. The configuration of this operation is not particularly limited, and any methods that do not require an operation different from a normal workflow in radiographic imaging can be employed. If the method is executable as part of the normal workflow, it leads to improved operator usability.

For example, according to Japanese Patent Application Laid-Open No. 2013-236711, wireless communication settings are made in combination with an operation of inserting the radiographic imaging apparatus 110 into a cradle for charging. From this configuration, charging the radiographic imaging apparatus 110 as a workflow operation of the operator can be considered as a method of requesting a wireless connection request.

Further, in recent years, a communication method based on the NFC standards described as a configuration of the near-field wireless communication connection apparatus 101 has been used in a power feeding system, i.e., a power feeding apparatus including a power feeding coil that contactlessly outputs power and a power reception apparatus including a power reception coil that contactlessly receives power fed from the power feeding apparatus.

Thus, in the radiographic imaging system having a configuration according to the second example embodiment, the configuration of the near-field wireless communication connection apparatus 101 of the radiographic imaging control apparatus 100 uses the NFC standards, and a power reception apparatus and a power feeding apparatus are added to the radiographic imaging apparatus 110 and the near-field wireless communication connection apparatus 101, respectively. Furthermore, the processing of a wireless connection request from the operator in the radiographic imaging system is changed. Only differences from the first example embodiment will be described below with reference to FIGS. 6 to 8.

Figure 6:
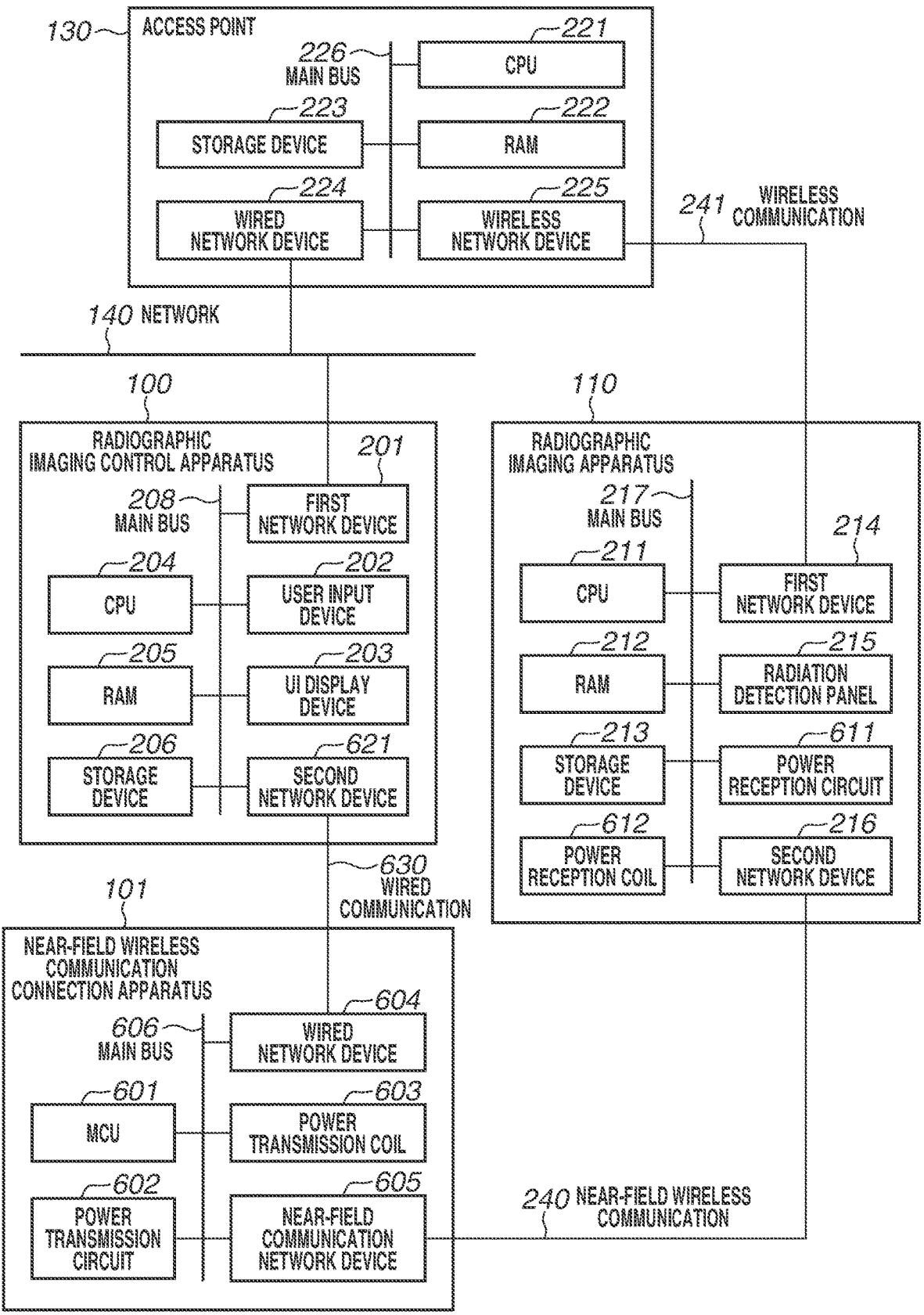
FIG. 6 is a diagram illustrating an example of a hardware configuration of a radiographic imaging system according to a second example embodiment.

FIG. 6 is a diagram illustrating an example of a hardware configuration of the radiographic imaging system according to the present example embodiment, which includes the near-field wireless communication connection apparatus 101 in addition to the radiographic imaging control apparatus 100, the radiographic imaging apparatus 110, and the access point 130. The radiographic imaging control apparatus 100 includes a second network apparatus 621 that performs the changed processing. The radiographic imaging apparatus 110 further includes a power reception circuit 611 and a power reception coil 612.

The radiographic imaging control apparatus 100 includes the second network apparatus 621. The second network apparatus 621 communicates with the near-field wireless communication connection apparatus 101 through wired communication 630 based on a communication protocol for wired communication connection (universal serial bus (USB), Recommended Standard 232 version C (RS-232C), or Ethernet®).

The near-field wireless communication connection apparatus 101 includes a micro controller unit (MCU) 601 and a wired network apparatus 604. The MCU 601 controls the entire near-field wireless communication connection apparatus 101. The wired network apparatus 604 communicates with the radiographic imaging control apparatus 100 through the wired communication 630 based on the communication protocol for wired communication connection.

The near-field wireless communication connection apparatus 101 further includes a power transmission circuit 602 and a power transmission coil 603.

The power transmission circuit 602 is a circuit having a function of adjusting an alternating current signal generated by the power transmission circuit 602 to an alternating current signal having predetermined power and outputting the adjusted alternating current signal.

The power transmission coil 603 transmits the alternating current signal of power generated by the power transmission circuit 602 to the power reception coil 612 of the radiographic imaging apparatus 110 based on a communication protocol such as the Qi or NFC standards. While the power transmission coil 603 is prepared for the alternating current signal transmission according to the present exemplary embodiment, the alternating current signal of power generated by the power transmission circuit 602 may be shared between a near-field communication network device 605 and the power transmission coil 603, and the shared alternating current signal may be transmitted from the near-field communication network device 605 to the second network device 216 of the radiographic imaging apparatus 110, by using the NFC standards.

The near-field wireless communication connection apparatus 101 further includes the near-field communication network device 605. The near-field communication network device 605 communicates with the radiographic imaging apparatus 110 through the near-field wireless communication 240 based on the communication protocol for near-field wireless communication connection.

The components of the near-field wireless communication connection apparatus 101 are connected together via a main bus 606 and can transmit and receive data to and from one another.

The radiographic imaging apparatus 110 further includes the power reception circuit 611 and the power reception coil 612.

The power reception circuit 611 is a circuit having a function of converting the alternating current signal of power received from the power reception coil 612 into a certain voltage by matching the power feeding frequency and transmitting the voltage to a battery (not illustrated) of the radiographic imaging apparatus 110.

The power reception coil 612 contactlessly receives the alternating current signal transmitted from the power transmission coil 603 of the near-field wireless communication connection apparatus 101 based on the communication protocol such as the Qi or NFC standards. While the power reception coil 612 is prepared for the alternating current signal reception according to the present exemplary embodiment, the received alternating current signal may be shared between the second network device 216 and the power reception coil 612 by using the NFC standards.

Figure 7:
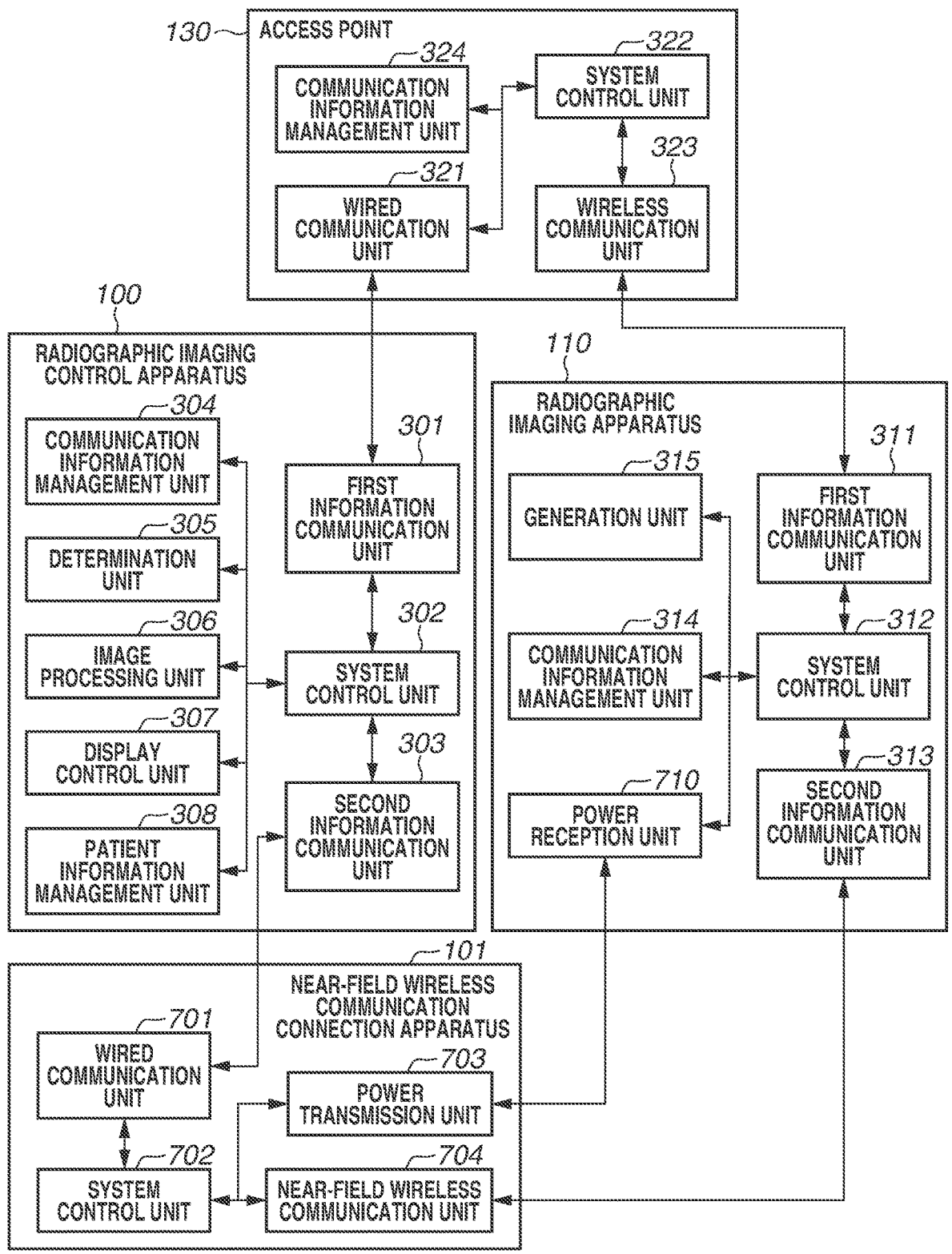
FIG. 7 is a diagram illustrating an example of a software configuration of the radiographic imaging system according to the second example embodiment.

FIG. 7 is a diagram illustrating an example of a software configuration of the radiographic imaging system according to the present example embodiment, which includes the near-field wireless communication connection apparatus 101 in addition to the radiographic imaging control apparatus 100, the radiographic imaging apparatus 110, and the access point 130. The radiographic imaging apparatus 110 further includes a power reception unit 710.

The MCU 601 reads a stored control program and executes the read program to realize the functional units of the near-field wireless communication connection apparatus 101.

The near-field wireless communication connection apparatus 101 includes a wired communication unit 701, a system control unit 702, a power transmission unit 703, and a near-field wireless communication unit 704.

The wired communication unit 701 is software that controls the wired network apparatus 604 to perform wired communication.

The system control unit 702 transmits and receives various types of setting information for the radiographic imaging apparatus 110 to and from the radiographic imaging control apparatus 100 via the wired communication unit 701. Further, the system control unit 702 transmits the alternating current signal of power to the radiographic imaging apparatus 110 via the power transmission unit 703 and transmits and receives various types of setting information to and from the radiographic imaging apparatus 110 via the near-field wireless communication unit 704.

Furthermore, the system control unit 702 is a program for realizing basic functions of the near-field wireless communication connection apparatus 101 and controls operation of each component of the near-field wireless communication connection apparatus 101.

The radiographic imaging apparatus 110 further includes the power reception unit 710.

The power reception unit 710 receives the alternating current signal of power via the power reception coil 612. In the reception, the system control unit 312 controls the power reception circuit 611 and stores power in the battery (not illustrated) of the radiographic imaging apparatus 110.

FIG. 8 is a sequence diagram illustrating a process of wireless information communication between the radiographic imaging control apparatus 100 and the radiographic imaging apparatus 110 using the near-field wireless communication connection apparatus 101.

In step S801, the operator (not illustrated) such as the user performs an operation to issue a wireless power feeding request to the radiographic imaging apparatus 110. According to the present example embodiment, the operation to issue a wireless power feeding request is performed by bringing the radiographic imaging apparatus 110 near the near-field wireless communication connection apparatus 101 in a contactless state. The configuration, however, is not particularly limited, and any operations by which the radiographic imaging apparatus 110 can receive the alternating current signal of power from the near-field wireless communication connection apparatus 101 can be employed, e.g., an operation of placing the radiographic imaging apparatus 110 on the near-field wireless communication connection apparatus 101.

In step S802, the near-field wireless communication connection apparatus 101 transmits the alternating current signal of power to the radiographic imaging apparatus 110 via the power transmission unit 703. According to the present example embodiment, the near-field wireless communication connection apparatus 101 regularly transmits the alternating current signal of power a plurality of times at uniform intervals. Alternatively, for example, the transmission of the alternating current signal of power can be started after the placement of the radiographic imaging apparatus 110 on the near-field wireless communication connection apparatus 101 is detected and performed a plurality of times at uniform intervals.

Upon the reception of the alternating current signal of power by the radiographic imaging apparatus 110 via the power reception unit 710 in step S802, step S403 and subsequent steps according to the first example embodiment are performed.

After step S409 is performed, the radiographic imaging apparatus 110 simultaneously performs processing with respect to the operator (not illustrated), processing with respect to the access point 130, and processing with respect to the radiographic imaging apparatus 110. The processing performed with respect to the access point 130 in step S411 is similar to that in the first example embodiment.

In step S803, the radiographic imaging apparatus 110 provides a request response indicating the completion of the operation of issuing a wireless power feeding request to the operator (not illustrated). According to the present example embodiment, the request response is provided by lighting the display portion (not illustrated), such as a LED, of the radiographic imaging apparatus 110. The configuration, however, is not particularly limited, and any methods of providing a request response to the operator can be employed, e.g., the radiographic imaging apparatus 110 can output a sound as a request response.

In step S804, the radiographic imaging apparatus 110 starts storing the alternating current signal of power received via the power reception unit 710 in the battery (not illustrated) of the radiographic imaging apparatus 110 using the system control unit 312.

As described above, according to the second example embodiment, an operator such as a user can make settings for performing wireless communication between a desired radiographic imaging control apparatus and a radiographic imaging apparatus in performing a wireless power feeding operation. This improves operator usability in making the settings for performing wireless communication.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While to example embodiments have been described, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2020-196898, filed Nov. 27, 2020, which is hereby incorporated by reference herein in its entirety.

What is claimed is:

1. A radiographic imaging system comprising:
a radiographic imaging apparatus configured to capture a radiographic image; and
a radiographic imaging control apparatus configured to connect to the radiographic imaging apparatus wirelessly and control image capturing performed by the radiographic imaging apparatus,
wherein the radiographic imaging control apparatus includes:
a first Bluetooth interface; and
one or more first controllers configured to:
receive two or more radio waves transmitted from the radiographic imaging apparatus via the first Bluetooth interface, the two or more radio waves requesting a connection through Bluetooth communication;
acquire wireless information for establishing a network connection with the radiographic imaging apparatus in a case where the received two or more radio waves requesting the connection satisfy a predetermined condition for stable reception of the two or more radio waves; and
transmit the wireless information to the radiographic imaging apparatus, and
wherein the radiographic imaging apparatus includes:
a second Bluetooth interface;
a wireless network interface; and
one or more second controllers configured to:
transmit the two or more radio waves requesting the connection through the second Bluetooth interface to the radiographic imaging control apparatus;
set a setting of the wireless network interface to establish the network connection based on the wireless information received from the radiographic imaging control apparatus; and
capture a radiographic image based on control by the radiographic imaging control apparatus connected based on the setting,
wherein the one or more first controllers are further configured to determine whether the two or more radio waves requesting the connection satisfy the predetermined condition based on whether the two or more radio waves that each have a signal intensity greater than or equal to a predetermined value are received a predetermined number of times or more or based on whether an average of the signal intensities of the two or more radio waves received the predetermined number of times is greater than or equal to a threshold value.

2. The radiographic imaging system according to claim 1, wherein the one or more first controllers are further configured to determine whether the two or more radio waves received by the first Bluetooth interface are radio waves each including at least one of an identification that is a corporate identifier identifying a corporate by which the radiographic imaging apparatus is manufactured and an identification that is a unique serial number of the radiographic imaging apparatus.

3. The radiographic imaging system according to claim 1, wherein the wireless information includes information for identifying a communication network.

4. The radiographic imaging system according to claim 3, wherein the wireless information includes extended service set identifier (ESSID) information or physical channel information.

5. A radiographic imaging system comprising:
a radiographic imaging apparatus configured to capture a radiographic image; and
a radiographic imaging control apparatus configured to connect to the radiographic imaging apparatus wirelessly and control image capturing performed by the radiographic imaging apparatus,
wherein the radiographic imaging control apparatus includes:
a first Bluetooth interface; and
one or more first controllers configured to:
receive two or more radio waves transmitted from the radiographic imaging apparatus via the first Bluetooth interface, the two or more radio waves requesting a connection through Bluetooth communication;
acquire wireless information for establishing a network connection with the radiographic imaging apparatus in a case where the received two or more radio waves requesting the connection satisfy a predetermined condition for stable reception of the two or more radio waves; and
transmit the wireless information to the radiographic imaging apparatus, and
wherein the radiographic imaging apparatus includes:
a second Bluetooth interface;
a wireless network interface; and
one or more second controllers configured to:
transmit the two or more radio waves requesting the connection through the second Bluetooth interface to the radiographic imaging control apparatus;
set a setting of the wireless network interface to establish the network connection based on the wireless information received from the radiographic imaging control apparatus; and
capture a radiographic image based on control by the radiographic imaging control apparatus connected based on the setting,
wherein the one or more first controllers are further configured to determine whether the two or more radio waves requesting the connection satisfy the predetermined condition based on whether the two or more radio waves that each have a signal intensity greater than or equal to a threshold value are received a predetermined number of times within a predetermined time or whether an average of a reception interval of the two or more radio waves received the predetermined number of times is within a predetermined time.

6. A radiographic imaging system comprising:
a radiographic imaging apparatus configured to capture a radiographic image; and
a radiographic imaging control apparatus configured to connect to the radiographic imaging apparatus wirelessly and control image capturing performed by the radiographic imaging apparatus, wherein the radiographic imaging control apparatus includes:
a first Bluetooth interface; and
one or more first controllers configured to:
receive two or more radio waves transmitted from the radiographic imaging apparatus via the first Bluetooth interface, the two or more radio waves requesting a connection through Bluetooth communication;
acquire wireless information for establishing a network connection with the radiographic imaging apparatus in a case where the received two or more radio waves requesting the connection satisfy a predetermined condition for stable reception of the two or more radio waves; and
transmit the wireless information to the radiographic imaging apparatus, and
wherein the radiographic imaging apparatus includes:
a second Bluetooth interface;
a wireless network interface; and
one or more second controllers configured to:
transmit the two or more radio waves requesting the connection through the second Bluetooth interface to the radiographic imaging control apparatus;
set a setting of the wireless network interface to establish the network connection based on the wireless information received from the radiographic imaging control apparatus; and
capture a radiographic image based on control by the radiographic imaging control apparatus connected based on the setting,
wherein the one or more first controllers are further configured to measure range information from the two or more radio waves requesting the connection that satisfy a predetermined reception condition value based on whether detected range information less than or equal to a threshold value is received a predetermined number of times or whether an average of the pieces of detected range information received the predetermined number of pieces of times is less than or equal to a threshold value.

7. A method of controlling a radiographic imaging system comprising a radiographic imaging apparatus configured to capture a radiographic image and a radiographic imaging control apparatus configured to connect to the radiographic imaging apparatus wirelessly and control image capturing performed by the radiographic imaging apparatus, the method comprising:
transmitting two or more radio waves requesting a connection through Bluetooth communication from the radiographic imaging apparatus to the radiographic imaging control apparatus;
receiving the two or more radio waves requesting the connection through the Bluetooth transmitted from the radiographic imaging apparatus by the radiographic imaging control apparatus;
acquiring wireless information for establishing a network connection with the radiographic imaging apparatus by the radiographic imaging control apparatus in a case where the received two or more radio waves requesting the connection satisfies a predetermined condition for stable reception of the two or more radio waves;
transmitting the wireless information to the radiographic imaging apparatus by the radiographic imaging control apparatus;
setting a setting of a wireless network interface of the radiographic imaging apparatus to establish the network connection based on the wireless information received from the radiographic imaging control apparatus by the radiographic imaging apparatus; and
capturing a radiographic image by the radiographic imaging apparatus based on control by the radiographic imaging control apparatus connected based on the setting,
wherein the acquiring includes determining whether the two or more radio waves requesting the connection satisfy the predetermined condition based on whether the two or more radio waves that each have a signal intensity greater than or equal to a predetermined value are received a predetermined number of times or based on whether an average of the signal intensities of the two or more radio waves received the predetermined number of times is greater than or equal to a threshold value.

8. A non-transitory storage medium storing a program for causing a computer to execute the method of controlling a radiographic imaging system according to claim 7.

9. A radiographic imaging system comprising
a radiographic imaging apparatus configured to capture a radiographic image; and
a radiographic imaging control apparatus configured to connect to the radiographic imaging apparatus wirelessly and control image capturing performed by the radiographic imaging apparatus,
wherein the radiographic imaging control apparatus includes:
a first Near Field Communication (NFC) interface;
a power transmission portion configured to transmit power to the radiographic imaging apparatus; and
one or more first controllers configured to:
receive a radio wave transmitted from the radiographic imaging apparatus via the first NFC interface, the radio wave requesting a connection through NFC communication;
acquire wireless information for establishing a network connection with the radiographic imaging apparatus in a case where the received radio wave requesting the connection satisfies a predetermined condition; and
transmit the wireless information to the radiographic imaging apparatus, and
wherein the radiographic imaging apparatus includes:
a second NFC interface;
a power reception portion configured to receive power contactlessly;
a wireless network interface; and
one or more second controllers configured to:
transmit the radio wave requesting the connection through the second NFC interface to the radiographic imaging control apparatus;
set a setting of the wireless network interface to establish the network connection based on the wireless information received from the radiographic imaging control apparatus; and
capture a radiographic image based on control by the radiographic imaging control apparatus connected based on the setting, and
wherein in a case where the power reception portion detects the receipt of the power, the one or more controllers transmit the radio wave requesting the connection through the Near Field Communication to the radiographic imaging control apparatus.

10. The radiographic imaging system according to claim 9, wherein the power reception portion of the radiographic imaging apparatus and the power transmission portion of the radiographic imaging control apparatus communicate with each other using a communication method based on a Near Field Communication (NFC) standard.

11. The radiographic imaging system according to claim 9, wherein the wireless information includes information for identifying a communication network.

12. The radiographic imaging system according to claim 10, wherein the one or more first controllers are further configured to determine whether the radio wave received by the first NFC interface is a radio wave including at least one of an identification that is a corporate identifier identifying a corporate by which the radiographic imaging apparatus is manufactured and an identification that is a unique serial number of the radiographic imaging apparatus.

13. The radiographic imaging system according to claim 11, wherein the wireless information includes extended service set identifier (ESSID) information or physical channel information.

* * * * *